(12) United States Patent
Rubinfeld et al.

(10) Patent No.: US 6,613,753 B2
(45) Date of Patent: Sep. 2, 2003

(54) RESTORE CANCER-SUPPRESSING FUNCTIONS TO NEOPLASTIC CELLS THROUGH DNA HYPOMETHYLATION

(75) Inventors: Joseph Rubinfeld, Danville, CA (US); Lucy Chang, San Mateo, CA (US); Jorge DiMartino, San Carlos, CA (US)

(73) Assignee: SuperGen, Inc., Dublin, CA (US)

( * ) Notice: Subject to any disclaimer, the term of this patent is extended or adjusted under 35 U.S.C. 154(b) by 30 days.

(21) Appl. No.: 09/790,483

(22) Filed: Feb. 21, 2001

(65) Prior Publication Data

US 2002/0114809 A1 Aug. 22, 2002

(51) Int. Cl.[7] .................. A01N 43/04; A01N 55/02; A61K 31/70; A61K 31/28
(52) U.S. Cl. ........................... 514/49; 514/492
(58) Field of Search .................... 514/49, 492

(56) References Cited

PUBLICATIONS

Lenzi et al. (International Jnl. Oncology, 1995, vol. 6 (2), pp. 447–450).*
Schwartsmann et al. (Investigational New Drugs, Feb. 2000, vol. 18 (1), pp. 83–91).*
Plumb et al. (Cancer Research, vol. 60, pp. 6039–6044, Nov. 1, 2000).*
Kritz, et al.; "Pilot Study of 5–Azacytidine (5–AZA) and Carboplatin (CBDCA) in Patients with Relapsed/Refractory Leukemia"; Am. J. Hematol, Feb. 1996, vol. 5, No. 2; Abstract.
Colombo, et al., "Antagonism of 5–aza–2'–Deoxycytidine Antileukemic Activity by Concomitant Treatment with Cytarabine"; Cancer Treatment Rep., Dec. 1986, vol. 70, No. 12; Abstract.
Momparler, et al., "Effect of 5–aza–2'–Deoxycytidine and Retinoic Acid on Differentiation and C–Myc Expression in HL–60 Myeloid Leukemic Cells"; Cancer Lett, Oct. 1990, vol. 54, No. 1–2; Abstract.
Anzai, et al., "Synergistic Cytotoxicity with 2'–Deoxy–5–Azacytidine and Topotecan in Vitro and in Vivo"; Cancer Res., Apr. 1992, vol. 52, No. 8; Abstract.
Dore, et al., "Effects of 5–Aza–2'–Deoxycytidine and Interferon–Alpha on Differentiation and Oncogene Expression in HL–60 myeloid Leukemic Cells"; Anticancer Drugs, Jun. 1992, vol. 3, No. 3; Abstract.
Schwartsmann, et al.; "Decitabine (5–Aza–2'–Deoxycytidine;DAC) Plus Daunorubicin as a First Line Treatment in Patients with Acute Myeloid Leukemia: Preliminary Observations"; Leukemia, Mar. 1997, vol. 11, Suppl. 1; Abstract.
Willemze, et al., "A Randomized Phase II Study on the Effects of 5–Aza–2'–Deoxycytidine Combined with Either Amsacrine or Idarubicin in Patients with Relapsed Acute Leukemia; an EORTC Leukemia Cooperative Group Phase II Study"; Leukemia, Mar. 1997, vol. 11, Suppl. 1; Abstract.

* cited by examiner

*Primary Examiner*—Anthony C. Caputa
*Assistant Examiner*—Gary B. Nickol
(74) *Attorney, Agent, or Firm*—Shirley Chen & Maya Skubatch; Wilson Sonsini; Goodrich & Rosati

(57) ABSTRACT

Compositions and methods are provided for treating diseases associated with abnormal cell proliferation such as cancer by storing inherent tumor-suppressing functions of neoplastic cells through DNA hypomethylation. The method comprises: delivering to a patient suffering from cancer a therapeutically effective amount of a DNA methylation inhibitor such as decitabine, in combination with an effective amount of an anti-neoplastic agent whose activity as an anti-neoplastic agent in vivo is adversely affected by aberrant DNA methylation. The anti-neoplastic agent can be an alkylating agent, an antibiotic agent, an antimetabolic agent, a retinoid, a hormonal agent, a plant-derived agent, an anti-angiogenesis agent and a biologic agent such as monoclonal antibody and interferon.

13 Claims, No Drawings

RESTORE CANCER-SUPPRESSING FUNCTIONS TO NEOPLASTIC CELLS THROUGH DNA HYPOMETHYLATION

BACKGROUND OF THE INVENTION

1. Field of the Invention

This invention relates to compositions and methods for using antineoplastic agents to treat diseases associated with abnormal cell proliferation such as cancer, and more specifically, to compositions and methods for improving the effectiveness of antineoplastic agents in treating cancer by restoring inherent tumor-suppressing functions of neoplastic cells through DNA hypomethylation.

2. Description of Related Art

A wide variety of antineoplastic agents have been developed to treat cancer. Examples of anti-neoplastic agents include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Additional examples of anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormiaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Although thousands of potential anticancer agents have been evaluated, the treatment of human cancer remains fraught with complications and side effects which often present an array of suboptimal treatment choices. Despite the great number of anti-neoplastic agents that are used in the clinic for cancer treatment, a need still exists for more effective drug regimens for treating cancer in a more genetically specific manner. The present invention relates to one such improved drug regimen for treating cancer, especially malignant solid tumors.

SUMMARY OF THE INVENTION

The present invention provide new and improved compositions, kits, and methods for treating cancers using a combination therapy which includes a DNA methylation inhibitor, and an anti-neoplastic agent whose activity as an anti-neoplastic agent in vivo is adversely affected by high levels of DNA methylation.

In one embodiment, the DNA methylation inhibitor is a cytidine analog. In a preferred variation of this embodiment, the DNA methylation inhibitor is 5-aza-2'-deoxycytidine (5-aza-CdR or decitabine).

In one embodiment, the anti-neoplastic agent is an alkylating agent. Examples of alkylating agents include, but are not limited to bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), non-classic alkylating agents (altretamine, dacarbazine, and procarbazine), platinum compounds (carboplastin and cisplatin).

In a variation of the embodiment, the anti-neoplastic agent is cisplatin or carboplastin.

In another variation of the embodiment, the anti-neoplastic agent is cyclophosphamide.

In another embodiment, the anti-neoplastic agent is a member of the retinoids superfamily. Retinoids are a family of structurally and functionally related molecules that are derived or related to vitamin A (all-trans-retinol). Examples of retinoid include, but are not limited to, all-trans-retinol, all-trans-retinoic acid (tretinoin), 13-cis retinoic acid (isotretinoin) and 9-cis-retinoic acid.

In yet another embodiment, the anti-neoplastic agent is an antibiotic agent. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin.

In yet another embodiment, the anti-neoplastic agent is a hormonal agent. Examples of such a hormonal agent are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

In yet another embodiment, the anti-neoplastic agent is a plant-derived agent. Examples of plant-derived agents include, but are not limited to, vinca alkaloids (e.g., vincristine, vinblastine, vindesine, vinzolidine and vinorelbine), camptothecin (20(S)-camptothecin, 9-nitro-20 (S)-camptothecin, and 9-amino-20(S)-camptothecin), podophyllotoxins (e.g., etoposide (VP-16) and teniposide (VM-26)), and taxanes (e.g., paclitaxel and docetaxel).

In yet another embodiment, the anti-neoplastic agent is a biologic agent. Examples of biologic agents include, but are not limited to, immuno-modulating proteins such as cytokines, monoclonal antibodies against tumor antigens, tumor suppressor genes, and cancer vaccines.

Examples of interleukins that may be used in conjunction with the DNA methylation inhibitor include, but are not limited to, interleukin 2 (IL-2), and interleukin 4 (IL-4), interleukin 12 (IL-12). Examples of interferons that may be used in conjunction with the DNA methylation inhibitor include, but are not limited to, interferon α, interferon β (fibroblast interferon) and interferon γ (fibroblast interferon). Examples of such cytokines include, but are not limited to erythropoietin (epoietin α), granulocyte-CSF (filgrastim), and granulocyte, macrophage-CSF (sargramostim). Immuno-modulating agents other than cytokines include, but are not limited to bacillus Calmette-Guerin, levamisole, and octreotide.

Example of monoclonal antibodies against tumor antigens that can be used in conjunction with the DNA methylation inhibitor include, but are not limited to, HERCEPTIN® (Trastruzumab), RITUXAN® (Rituximab), MYELO-TARG® (anti-CD33), and CAMPATH® (anti-CD52).

The compositions, kits and methods of the present invention may be used to treat a wide variety of indications for which the second anti-neoplastic agent has therapeutic activity. Such indications include various types of cancers including, but not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

The compositions, kits and methods of the present invention may also be used to treat various hematological disorders for which the second anti-neoplastic agent has therapeutic activity. Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, chronic lymphoblastic leukemia, Hodgkins disease, Non-Hodgkin Lymphomas, the myelodysplastic syndromes, and sickle cell anemia.

In regard to the compositions of the present invention, the compositions may comprise a DNA methylation inhibitor such as decitabine in combination with one or more antineoplastic agent(s). In one particular embodiment, the anti-neoplastic agent is cisplatin, retinoid, or mitomycin C.

In regard to the kits of the present invention, the kits may comprise a DNA methylation inhibitor such as decitabine in combination with one or more antineoplastic agent(s). In one particular embodiment, the anti-neoplastic agent is cisplatin, retinoid, or mitomycin C.

In regard to the methods of the present invention, the method may comprise administering to a patient with cancer a therapeutically effective amount of a DNA methylation inhibitor such as decitabine, and an anti-neoplastic agent. The DNA methylation inhibitor and the anti-neoplastic agent may be delivered separately or in combination. In one embodiment, the DNA methylation inhibitor is delivered prior to delivering the anti-neoplastic agent.

The DNA methylation inhibitor and the anti-neoplastic agent may be delivered via various routes of administration. They may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

DETAILED DESCRIPTION OF THE INVENTION

The present invention provides new and improved compositions, kits, and methods for treating cancers using a combination therapy which includes a DNA methylation inhibitor, and an anti-neoplastic agent whose activity as an anti-neoplastic agent in vivo is adversely affected by high levels of DNA methylation.

Pharmaceutical activity of anti-neoplastic agents is believed to be adversely affected by aberrant hypermethylation of cancer-related genes. Due to hypermethylation of cancer-related genes, especially in the promoter regions of tumor suppressor genes, expression levels of these genes are lowered. Meanwhile, many antineoplastic agents exert their anti-cancer effects by triggering signal transduction cascades involving proteins encoded by these tumor suppressor genes. With insufficient expression of these genes in cancer cells, the anti-cancer effects of these anti-neoplastic agents may be severely reduced or completely eradicated. Thus, inhibition of the aberrant hypermethylation of cancer-related genes is believed to restore tumor-suppressing functions to cancer cells in response to signals sent by the anti-neoplastic agent administered to the cancer patient.

In addition, the method of the present invention may also be used to enhance immunotherapy for cancer through inhibition of aberrant hypermethylation of certain genes associated with tumor cell surface antigen presentation. It is believed that tumor or leukemic cells evade immune detection and/or eradication by down-regulating cell surface antigens, at least partially through methylation of the genes encoding the target antigen. Inhibition of such hypermethylation and silencing of target antigen gene expression should boost therapeutic efficacy of immunotherapy targeting tumor-specific antigens. Examples of immunotherapy include, but are not limited to monoclonal antibodies targeting tumor-specific antigens, donor lymphocytes for inducing remission via a graft versus leukemia effect (GVL).

In one embodiment, the DNA methylation inhibitor is a cytidine analog. In a preferred variation of this embodiment, the DNA methylation inhibitor is 5-aza-2'-deoxycytidine (5-aza-CdR or decitabine).

1. Aberrant Hypermethylation of Cancer-Related Genes

In mammalian cells, approximately 3% to 5% of the cytosine residues in genomic DNA are present as 5-methylcytosine. Ehrlich et al (1982) Nucleic Acid Res. 10:2709–2721. This modification of cytosine takes place after DNA replication and is catalyzed by DNA methyltransferase using S-adenosyl-methionine as the methyl donor. Approximately 70% to 80% of 5-methylcytosine residues are found in the CpG sequence. Bird (1986) Nature 321:209–213. This sequence, when found at a high frequency, in the genome, is referred to as CpG islands. Unmethylated CpG islands are associated with housekeeping genes, while the islands of many tissue-specific genes are methylated, except in the tissue where they are expressed. Yevin and Razin (1993) in DNA Methylation: Molecular Biology and Biological Significance. Basel: Birkhauser Verlag, p523–568. This methylation of DNA has been proposed to play an important role in the control of expression of different genes in eukaryotic cells during embryonic development. Consistent with this hypothesis, inhibition of DNA methylation has been found to induce differentiation in mammalian cells. Jones and Taylor (1980) Cell 20:85–93.

Methylation of DNA in the regulatory region of a gene can inhibit transcription of the gene. This may be because 5-methylcytosine protrudes into the major groove of the DNA helix, which interferes with the binding of transcription factors.

The methylated cytosine in DNA, 5-methylcytosine, can undergo spontaneous deamination to form thymine at a rate much higher than the deamination of cytosine to uracil. Shen et al. (1994) Nucleic Acid Res. 22:972–976. If the deamination of 5-methylcytosine is unrepaired, it will result in a C to T transition mutation. For example, many "hot spots" of DNA damages in the human p53 gene are associated with CpG to TpG transition mutations. Denissenko et al. (1997) Proc. Natl. Acad. Sci. USA 94:3893–1898.

Other than the p53 gene, many tumor suppressor genes can also be inactivated by aberrant methylation of the CpG islands in their promoter regions. Many tumor-suppressors and other cancer-related genes have been found to be hypermethylated in human cancer cells and primary tumors. Examples of genes that participate in suppressing tumor growth and are silenced by aberrant hypermethylation include, but are not limited to, tumor suppressors such as p15/INK4B (cyclin kinase inhibitor, p16/INK4A (cyclin kinase inhibitor), p73 (p53 homology), ARF/INK4A (regular level p53), Wilms tumor, von Hippel Lindau (VHL), retinoic acid receptor-β (RARβ), estrogen receptor, androgen receptor, mammary-derived growth inhibitor hypermethylated in cancer (HIC1), and retinoblastoma (Rb); Invasion/metastasis suppressor such as E-cadherin, tissue inhibitor metalloproteinase-2 (TIMP-3), mts-1 and CD44; DNA repair/detoxify carcinogens such as methylguanine methyltransferase, hMLH1 (mismatch DNA repair), glutathione S-transferase, and BRCA-1; Angiogenesis inhibitors such as thrombospondin-1 (TSP-1) and TIMP3; and tumor antigens such as MAGE-1.

In particular, silencing of p16 is frequently associated with aberrant methylation in many different types of cancers. The p16/INK4A tumor suppressor gene codes for a constitutively expressed cyclin-dependent kinase inhibitor, which plays a vital role in the control of cell cycle by the cyclin D-Rb pathway. Hamel and Hanley-Hyde (1997) Cancer Invest. 15:143–152. P16 is located on chromosome 9p, a site that frequently undergoes losss of heterozygosity (LOH) in primary lung tumors. In these cancers, it is postulated that the mechanism responsible for the inactivation of the non-deleted allele is aberrant methylation. Indeed, for lung carcinoma cell lines that did not express p16, 48% showed signs of methylation of this gene. Otterson et al. (1995) Oncogene 11:1211–1216. About 26% of primary non-small cell lung tumors showed methylation of p16. Primary tumors of the breast and colon display 31% and 40% methylation of p16, respectively. Herman et al. (1995) Cancer Res. 55:4525–4530.

Aberrant methylation of retinoic acid receptors are also attributed to development of breast cancer, lung cancer, ovarian cancer, etc. Retinoic acid receptors are nuclear transcription factors that bind to retinoic acid responsive elements (RAREs) in DNA to activate gene expression. In particular, the putative tumor suppressor RARβ gene is located at chromosome 3p24, a site that shows frequent loss of heterozygosity in breast cancer. Deng et al. (1996) Science 274:2057–2059. Transfection of RARβ cDNA into some tumor cells induced terminal differentiation and reduced their tumorigenicity in nude mice. Caliaro et al. (1994) Int. J. Cancer 56:743–748; and Houle et al. (1993) Proc. Natl. Acad. Sci. USA 90:985–989. Lack of expression of the RARβ gene has been reported for breast cancer and other types of cancer. Swisshelm et al. (1994) Cell Growth Differ. 5:133–141; and Crowe (1998) Cancer Res. 58:142–148. This reason for lack of expression of RARβ gene is attributed to hypermethylation of RARβ gene. Indeed, methylation of RARβ was detected in 43% of primary colon carcinomas and in 30% of primary breast carcinoma. Cote et al. (1998) Anti-Cancer Drugs 9:743–750; and Bovenzi et al. (1999) Anticancer Drugs 10:471–476.

Hypermethylation of CpG islands in the 5'-region of the estrogen receptor gene has been found in multiple tumor types. Issa et al. (1994) J. Natl. Cancer Inst. 85:1235–1240. The lack of estrogen receptor expression is a common feature of hormone unresponsive breast cancers, even in the absent of gene mutation. Roodi et al. (1995) J. Natl. Cancer Inst. 87:446–451. About 25% of primary breast tumors that were estrogen receptor-negative displayed aberrant methylation at one site within this gene. Breast carcinoma cell lines that do not express the mRNA for the estrogen receptor displayed increased levels of DNA methyltransferase and extensive methylation of the promoter region for this gene. Ottaviano et al. (1994) 54:2552–2555.

Hypermethylation of human mismatch repair gene (hMLH-1) is also found in various tumors. Mismatch repair is used by the cell to increase the fidelity of DNA replication during cellular proliferation. Lack of this activity can result in mutation rates that are much higher than that observed in normal cells. Modrich and Lahue (1996) Annu. Rev. Biochem. 65:101–133. Methylation of the promoter region of the mismatch repair gene (hMLH-1) was shown to correlate with its lack of expression in primary colon tumors, whereas normal adjacent tissue and colon tumors the expressed this gene did not show signs of its methylation. Kane et al. (1997) Cancer Res. 57:808–811.

The molecular mechanisms by which aberrant methylation of DNA takes place during tumorigenesis are not clear. It is possible that the DNA methyltransferase makes mistakes by methylating CpG islands in the nascent strand of DNA without a complementary methylated CpG in the parental strand. It is also possible that aberrant methylation may be due to the removal of CpG binding proteins that "protect" these sites from being methylated. Whatever the mechanism, the frequency of aberrant methylation is a rare event in normal mammalian cells.

2. Decitabine as an Inhibitor of DNA Methylation

Decitabine, 5-aza-2'-deoxycytidine, is an antagonist of its related natural nucleoside, deoxycytidine. The only structural difference between these two compounds is the presence of a nitrogen at position 5 of the cytosine ring in decitabine as compared to a carbon at this position for deoxycytidine. Two isomeric forms of decitabine can be distinguished. The β-anomer is the active form. The modes of decomposition of decitabine in aqueous solution are (a) conversion of the active b-anomer to the inactive α-anomer (Pompon et al. (1987) J. Chromat. 388:113–122); (b) ring cleavage of the aza-pyrimidine ring to form N-(formylamidino)-N'-β-D-2'-deoxy(ribofuranosy)-urea (Mojaverian and Repta (1984) J. Pharm. Pharmacol. 36:728–733); and (c) subsequent forming of guanidine compounds (Kissinger and Stemm (1986) J. Chromat. 353:309–318).

Decitabine possesses multiple pharmacological characteristics. At a molecular level, it is S-phase dependent for incorporation into DNA. At a cellular level, decitabine can induce cell differentiation and exert hematological toxicity. Despite having a short half life in vivo, decitabine has excellent tissue distribution.

The most prominent function of decitabine is its ability to specifically and potently inhibit DNA methylation. As described above for methylation of cytosine in CpG islands as an example, methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine. Momparler et al. (1985) 30:287–299. After conversion to its triphosphate form by deoxycytidine kinase, decitabine is incorporated into replicating DNA at a rate similar to that of the natural substrate, dCTP. Bouchard and Momparler (1983) Mol. Pharmacol. 24:109–114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) Proc. Natl. Acad. Sci. USA 91:11797–11801. By specifically inhibiting DNA methyltransferase, the enzyme required for methylation, the aberrant methylation of the tumor suppressor genes can be prevented.

According to the present invention, the inventors take advantage of the ability of DNA methylation inhibitors, such as decitabine, reactivate the tumor suppressor genes silenced by aberrant hypermethylation. By reducing hypermethylation, these agents cancer render more effective anti-neoplastic agents whose pharmaceutical activity are adversely affected by hypermethylation in vivo.

3. Combination of DNA Methylation Inhibitor with Retinoid

In a preferred embodiment, a DNA methylation inhibitor is used in combination with retinoid to treat patients with abnormal cell proliferative diseases such as cancer. In a more preferred embodiment, the combination therapy of decitabine and retinoid is used to treat breast cancer, colon cancer and lung cancer, in particular, non-small cell lung cancer.

Retinoids are a group of natural and synthetic vitamin A analogs and are promising agents for the prevention and treatment of a variety of cancers and diseases. The anti-cancer effects of retinoids are mainly mediated by their nuclear receptors, the retinoic acid receptors (RARs) and the retinoid X receptors (RXRs). Retinoids, such as trans-retinoic acid, effectively induce RARβ expression and inhibit the growth of hormone-dependent but not hormone-independent breast cancer cells. Induction of RARβ in hormone-dependent breast cancer cells is mediated by RAR/RXR heterodimer that binds to the RA response element (RARE) in the RARβ promoter. Expression of RARs and RXRs is not sufficient to render RARβ expression responsive to RA. Other transcription factors and/or adaptors may also be required for the RA-responsive transcription activation. In addition, if these factors have low binding affinity to the RARβ promoter, the expression levels of RARβ will be reduced, which renders the cancer cells unresponsive to RA. Indeed, retinoid responses are impaired in a majority of lung cancer cells and the loss of RARβ is primarily responsible for the defect.

The low expression levels or lack of expression of RARβ is believed to be attributed to aberrant hypermethylation of the promoter region of the RARβ gene. By inhibiting aberrant hypermethylation of the RARβ promoter using decitabine or another DNA methylation inhibitor, the RA-responsiveness of the cancer cells can be improved. The combination of decitabine and retinoid can have a synergistic effect on cancer cells in that retinoid induces apoptosis of cancer cells whose resistance to RA is suppressed by inhibition of hypermethylation of the RARβ promoter.

The retinoid that may be used in combination with decitabine may be a natural or synthetic retinoid that binds to retinoid acid receptors (RARs) and triggers RAR-mediated signal transduction. Examples of retinoid include, but are not limited to, all-trans-retinol, all-trans-retinoic acid (tretinoin), 13-cis retinoic acid (isotretinoin) and 9-cis-retinoic acid.

4. Combination of DNA Methylation Inhibitor with Cisplatin

In another preferred embodiment, a DNA methylation inhibitor is used in combination with cisplatin to treat patients with abnormal cell proliferative diseases such as cancer.

Cisplatin is an alkylating agent that forms a variety of DNA adducts which inhibit DNA replication transcription and induce apoptosis, presumably through DNA mismatch repair. The 1,2 d(GpG) intrastrand DNA adduct is the most common adduct found in vitro and in vivo. Cisplatin resistance in human cancer cells is associated with deficiency of DNA mismatch repair.

The low expression levels or lack of expression of the mismatch repair gene (e.g. hMLH-1) is believed to be attributed to aberrant hypermethylation of the promoter region of the mismatch repair gene. By inhibiting the aberrant hypermethylation of the promoter of the mismatch repair gene using decitabine or another DNA methylation inhibitor, the cisplatin-responsiveness of the cancer cells can be restored. The combination of decitabine and cisplatin can have a synergistic effect on cancer cells in that cisplatin alkylates DNA and induces apoptosis of cancer cells whose resistance to cisplatin is suppressed by inhibition of hypermethylation of the mismatch repair gene promoter.

Other alkylating agents may also be used in combination with a DNA methylation inhibitor to treat cancer patients. In one embodiment, the anti-neoplastic agent is an alkylating agent. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), non-classic alkylating agents (altretamine, dacarbazine, and procarbazine), and other platinum compounds (e.g., carboplastin).

5. Combination of DNA Methylation Inhibitor with Hormonal Agents

In a preferred embodiment, a DNA methylation inhibitor is used in combination with a hormonal agent to treat patients with abnormal cell proliferative diseases such as cancer. In a more preferred embodiment, the combination therapy of decitabine and hormonal agent is used to treat breast cancer, ovarian cancer, uterus cancer, prostate cancer and other types of cancers that are responsive to endocrine regulation.

Hormones play a pivotal role in regulating the growth and development of their target organs. Various hormonal agents have been used in the treatment of tumors originating from these target organs, namely the breast, uterus, ovary, and prostate. Most of the hormonal agents are sex steroids and their derivatives and analogs thereof, such as estrogens, androgens, and progestins. These hormonal agents may serve as antagonists of receptors for the sex steroids to down regulate transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including CPT and the hormonal agent may have therapeutic synergistic effects on cancer and reduce sides affects associated with these chemotherapeutic agents.

Estrogen, androgen, and progestins exert their function mainly through their respective receptors. After binding to the receptors in high affinity, the steroids alter the configuration of receptor molecules and make them capable of binding to a segment of DNA template called hormone response element, where the regulate gene transcription and control the cellular growth and function.

Many antagonists of these hormones have been developed in attempt to inhibit mitogenic effects associated with the interactions of these hormones with their cognate receptor in various tissues. Hormone responsiveness is a critical determinant of breast cancer progression and management, and the response to endocrine therapy is highly correlated with the estrogen receptor (ER) and progesterone receptor (PR) status of tumor cells. Most of the hormone antagonists function through competitive binding with the hormone receptors, which may result in altered conformations that differ from the active conformation required for stimulating cell growth. With such a "dead-locked" conformation, the receptor may participate in signal transduction pathways that lead to apoptosis of the cells. Thus, to render the cell responsive to these hormonal antagonist, it may be important to maintain sufficient levels of hormone receptors in cancer cells. However, in many cancer cells, expression of the hormone receptors are either down-regulated or altered to produce mutants of the receptor through different splicing mechanisms to render the mutant receptors lower binding affinity with these hormonal antagonists.

One-third of all breast cancers lack ER and PR; these conditions are associated with less differentiated tumors and poorer clinical outcome. In addition, approximately one-half of ER-positive tumors lack PR protein and patients with this phenotype are less likely to respond to hormonal therapies than those whose tumors express both receptors. Since PR is induced by ER; its presence is a marker of a functional ER.

For example, during the past 20 years, the hormonal therapy of choice for the treatment of breast cancer has been the antiestrogen, tamoxifen. The use of tamoxifen has been proved to produce a favorable response and survival advantage in patients whose tumors are classified as estrogen receptor-positive (ER+)/progesterone receptor-positive (PR+). Additionally, tamoxifen is the only drug known to reduce the incidence of contralateral disease. This drug produces relatively few harmful side effects, while exhibiting several beneficial effects such as maintaining bone density and reducing the incidence of myocardial infarction in the postmenopausal woman.

However, tumors eventually acquire a tamoxifen-resistant or tamoxifen-stimulated phenotype, resulting in disease recurrence. Several mechanisms have been proposed to account for tamoxifen-resistant breast cancer, in the hope of developing a more effective first-line or perhaps second-line treatment strategy. One theory is the occurrence of a mutation in the estrogen receptor, the drug target. A plethora of studies have reported the detection of estrogen receptor mRNA splice variants, and it has been suggested that the accumulation of these variant mRNAs are responsible for the development of tamoxifen-resistant breast cancer.

Other structural changes within ER and PR genes such as methylation, deletions, or polymorphisms are believed to contribute to the loss of ER and PR gene expression in breast cancer cells. In particular, the inventors believe that the low expression levels or lack of expression of the ER genes may be attributed to aberrant hypermethylation in the promoter region of these genes. Thus, by inhibiting the aberrant hypermethylation of the promoter of the ER genes using decitabine or another DNA methylation inhibitor, the hormone-responsiveness of the cancer cells can be restored. The combination of decitabine and the hormonal agent can have a synergistic effect on cancer cells in that the hormonal agent binds to the ER and induces apoptosis of cancer cells whose resistance to hormonal agent is suppressed by inhibition of hypermethylation of the ER promoter.

6. Combination of DNA Methylation Inhibitor with Immunotherapy

The present invention also provides methods of treating cancer with a DNA methylation inhibitor in conjunction with immunotherapy treatment.

In one embodiment, a DNA methylation inhibitor is used in combination with a monoclonal antibody against cancer cell surface antigen. Since tumor or leukemic cells evade immune detection and/or eradication by down-regulating cell surface antigens partially through methylation of the genes encoding the target antigen, Inhibition of such methylation and silencing of target antigen gene expression should boost therapeutic efficacy of immunotherapy targeting tumor-specific antigens.

As used herein, monoclonal antibodies against tumor antigens are antibodies elicited against antigens expressed by tumors and leukemic cells, preferably tumor-specific antigens. The monoclonal antibody also includes fully human and humanized antibody.

For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. In particular, metastatic breast cancer may evade such an immunotherapy by down-regulating expression of the HER2 protein through DNA methylation of this gene. Inhibition of DNA methylation of this gene by using decitabine, for example, should boost the expression of HER2 gene and enhance the therapeutic efficacy of the treatment with monoclonal antibody against this cell surface receptor (e.g., HERCEPTIN®). Therefore, combination therapy including a DNA methylation inhibitor and antibody targeting HER2 protein may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and maligant CD20+ pre-B and mature B cells. RITUXAN® is used as single agent for the treatment of patients with relapsed or refractory low-grade or follicular, CD20+ B cell non-Hodgkin's lymphoma. Combination therapy including a DNA methylation inhibitor and RITUXAN® may have therapeutic synergistic effects not only on lymphoma, but also on other forms or types of malignant tumors.

The DNA methylation inhibitor may also be used in combination with monoclonal antibodies targeting antigens expressed on the surface of lymphocytes. For example, CAMPATH® (alemtuzumab) is such a monoclonal antibody that specifically targets CD52 antigen that is found on B and T lymphocytes. This CD53 antibody binds to the lymphocytes and lyses them in several ways, including apoptosis. CAMPATH® is used for the treatment of chronic lymphocytic leukemia (CLL) and lymphoma. In particular, relapsed leukemia cells may evade the treatment of CAMPATH® by down-regulating expression of the CD52 antigen through DNA methylation of this gene. Inhibition of DNA methylation of this gene by using decitabine, for example, should boost the expression of CD52 antigen gene and enhance the therapeutic efficacy of the treatment with this antibody. Therefore, combination therapy including a DNA methylation inhibitor and antibody targeting CD52 antigen may have therapeutic synergistic effects on leukemia and lymphoma, thus reducing the toxicity to other non-target cells and reduces side effects significantly.

The DNA methylation inhibitor may also be used in combination with an antibody that is conjugated with a cytotoxic agent to selectively target and kill cancer cells expressing the antigen recognized by the antibody. For example, MYLOTARG® (Gemtuzumab zogamicin) is such an antibody conjugate that is indicated for the treatment of relapsed adult acute myelocytic leukemia. This antibody conjugate combines a specific antibody, CD33, with a chemotherapeutic drug (zogamicin). Specifically, the antibody attaches to the CD33 antigen found on leukemic cells which then delivers a toxic dose of zogamicin to the cancer cells. In particular, relapsed leukemia cells may develop resistance to the antibody conjugate by down-regulating expression of the CD33 antigen through DNA methylation of this gene. Inhibition of DNA methylation of this gene by using decitabine, for example, should boost the expression of CD33 antigen gene and enhance the therapeutic efficacy of the treatment with the antibody conjugate. Therefore, combination therapy including a DNA methylation inhibitor and antibody targeting CD33 antigen may have therapeutic synergistic effects on leukemia, especially on relapsed leukemia, thus reducing the toxicity to other non-target cells and reduces side effects significantly.

In another embodiment, a DNA methylation inhibitor is used in combination with donor lymphocyte infusion for the treatment of relapse post bone marrow transplant (BMT). Allogeneic BMT is standard of care for patients with chronic myeloid leukemia (CML). In some patients who relapse after BMT, infusion of allogeneic lymphocytes from the original bone marrow donor(s) can re-induce remission via a graft versus leukemia effect. Inhibition of DNA methylation by using decitabine, for example, should boost the expression of leukemia antigens and enhance the therapeutic efficacy of the donor lymphocytes. In a preferred embodiment, the patient is treated with decitabine prior to donor lymphocyte infusion.

In yet another embodiment, a DNA methylation inhibitor is used in combination with $^{131}$I for the treatment of thyroid cancer. Most thyroid cancers respond to $^{131}$I administered intravenously because thyroid cells possesses a highly specific sodium/iodine symporter (NIS) that efficiently takes up this radio chemical. In advanced or refractory thyroid cancer, cells have lost expression of this pump due to methylation and silencing of its gene. Combined treatment of thyroid cancer with a DNA methylation inhibitor, for example, decitabine, would obviate the loss of NIS expression and enhance therapeutic efficacy of $^{131}$I.

7. Other Anti-Neoplastic Agents Used in Combination

A wide variety of antineoplastic agents may be used in combination with a DNA methylation inhibitor such as decitabine for treating various diseases associated with abnormal cell proliferation such as cancer. The particular anti-neoplastic agent(s) combined with the DNA methylation inhibitor may depend on the particular type of cancer to be treated. The particular combinations described above are only illustrative examples of the present invention.

The antineoplastic agent may be an antibiotic agent. Antibiotic agents are a group of anticancer drugs that are produced in a manner similar to antibiotics by a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase 11 in the regions of transcriptionally active DNA, which leads to DNA strand scissions. Bleomycin is generally believed to chelate iron and form an activated complex, which then binds to bases of DNA, causing strand scissions and cell death. Combination therapy including decitabine and the antibiotic agent may have therapeutic synergistic effects on cancer and reduce sides affects associated with these chemotherapeutic agents.

The antineoplastic agent may be an antimetabolic agent. Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a DNA methylation inhibitor and the antimetabolic agent is believed therapeutic synergistic effects on cancer and reduce sides affects associated with these chemotherapeutic agents.

The antineoplastic agent may also be a plant-derived agent. Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), water soluble or insoluble camptothecin (e.g. 20(S)-camptothecin, 9-nitro-camptothecin, 9-nitro-camptothecin, and topotecan), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Camptothecin is believed to be a potent inhibitor of the nuclear enzyme DNA topoisomerase I (topo-I), which is responsible for "relaxation" of supercoiled double-stranded DNA by creating single-stranded breaks through which another DNA strand can pass during transcription. Topo-I reseals the break allowing DNA replication to occur. Inhibition of topo-I leads to the formation of stable DNA-topoisomerase complexes, with eventual formation of irreversible double-stranded DNA breaks, leading to apoptosis and/or other forms of cell death. Podophyllotoxins such as etoposide are believed to interfere with DNA synthesis by interacting with topoisomerase II, leading to DNA strand scission. Combination therapy including decitabine and the plant-derived agent may have therapeutic synergistic effects on cancer and reduce sides affects associated with these chemotherapeutic agents.

The antineoplastic agent may be a biologic agent. Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a DNA methylation inhibitor and the biologic agent may have therapeutic synergistic effects on cancer, enhance the patient's immune responses to tumorigenic signals, and reduce potential sides affects associated with this biologic agent.

Cytokines possess profound immunomodulatory activity. Some cytokines such as interleukin-2 (IL-2, aldesleukin) and interferon α (IFN-α) demonstrate antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with a DNA methylation inhibitor include, but are not limited to, interleukin 2 (IL-2), and interleukin 4 (IL-4), interleukin 12 (IL-12).

Interferon α includes more than 23 related subtypes with overlapping activities, all of the IFN-α subtypes within the scope of the present invention. IFN-α has demonstrated activity against many solid and hematologic malignancies, the later appearing to be particularly sensitive. Examples of interferons that may be used in conjunction with a DNA methylation inhibitor include, but are not limited to, interferon α, interferon β (fibroblast interferon) and interferon γ (fibroblast interferon).

Other cytokines that may be used in conjunction with a DNA methylation inhibitor include those cytokines that exert profound effects on hematopoiesis and immune functions. Examples of such cytokines include, but are not limited to erythropoietin (epoietin α), granulocyte-CSF (filgrastinm), and granulocyte, macrophage-CSF (sargramostim). These cytokines may be used in conjunction with a DNA methylation inhibitor to reduce chemotherapy-induced myelopoietic toxicity.

Immuno-modulating agents other than cytokines may also be used in conjunction with a DNA methylation inhibitor to inhibit abnormal cell growth. Examples of such immuno-modulating agents include, but are not limited to bacillus Calmette-Guerin, levamisole, and octreotide, a long-acting octapeptide that mimics the effects of the naturally occuring hormone somatostatin.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

8. Indications for Treatment

Preferable indications that may be treated using the compositions of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, chronic lymphoblastic leukemia, Hodgkins disease, Non-Hodgkin Lymphomas, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chormosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the t(15;17) chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanim of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired or abnormal angiogenesis. The method comprises administering to a patient suffering from undesired or abnormal angiogenesis a composition comprising a DNA methylation inhibitor, and an anti-neoplastic agent whose activity as an anti-neoplastic agent in vivo is adversely affected by high levels of DNA methylation. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the composition of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disese, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with abnormal angiogenesis. The method comprises administering to a patient suffering from a chronic inflammatory disease associated with abnormal angiogenesis a composition comprising a DNA methylation inhibitor, and an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the composition of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the composition of the present invention should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by the composition of the present invention should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the composition of the present invention to inhibit angionesis, such granulomas formation can be inhibited. Psoriasis, also a chronic and recurrent inflammatory disease, is characterized by papules and plaques of various sizes. Treatment using the composition of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the composition of the present invention alone or in conjunction with other anti-RA agents should prevent the formation of new blood vessels necessary to maintain the chronic inflammation and provide the RA patient relief from the symptoms.

9. Routes of Administration and Dosing Regimen

A wide variety of delivery methods and formulations for different delivery methods may be used in the combination therapies of the present invention.

The inventive combination of therapeutic agents may be administered as compositions that comprise the inventive combination of therapeutic agents. Such compositions may include, in addition to the inventive combination of therapeutic agents, conventional pharmaceutical excipients, and other conventional, pharmaceutically inactive agents. Additionally, the compositions may include active agents in addition to the inventive combination of therapeutic agents. These additional active agents may include additional compounds according to the invention, or one or more other pharmaceutically active agents. In preferable embodiments, the inventive compositions will contain the active agents, including the inventive combination of therapeutic agents, in an amount effective to treat an indication of interest.

The inventive combination of therapeutic agents and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The inventive combination of therapeutic agents and compositions may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time. For example, decitabine may be administered to a patient before, concomitantly, or after the antineoplastic agent is administered. In a preferred embodiment, the patient may be pretreated with the DNA methylation inhibitor (e.g., decitabine) and then treated with the anti-neoplastic agent.

Amounts of the inventive combination of therapeutic agents can vary, according to determinations made by one of skill, but preferably are in amounts effective to create a cytotoxic or cytostatic effect at the desired site. Preferably, these total amounts are less than the total amounts for systemic administration of the inventive combination of therapeutic agents, and are preferably less than the maximum tolerated dose. For the slow-release dosage form, appropriate release times can vary, but preferably should last from about 1 hour to about 6 months, most preferably from about 1 week to about 4 weeks. Formulations including the inventive combination of therapeutic agents and/or composition can vary, as determinable by one of skill, according to the particular situation, and as generally taught herein.

In a preferred embodiment, decitabine is administered to a patient by injection, such as bolus i.v. injection, continuous i.v. infusion and i.v. infusion over 1 hour. For example, decitabine may administered into the patient via an 1–24 hour i.v. infusion per day for 3–5 days per treatment cycle at a dose ranging from 1–1000 mg/m$^2$, preferably ranging from 1–200 mg/m$^2$, more preferably ranging from 2–50 mg/m$^2$, and most preferably from 5–20 mg/m$^2$. The preferred dosage below 50 mg/m$^2$ for decitabine is considered to be much lower than that used in conventional chemotherapy for cancer. By using such a low dose of decitabine, transcriptional activity of genes silenced in the cancer cells can be activated to trigger downstream signal transduction for cell growth arrest, differentiation and apoptosis. Such sensitization of cancer cells to cell death may require a lower dose of the anti-neoplastic agent used in conjunction with decitabine, thereby achieving a higher therapeutic index in the treatment. Moreover, lowering the dosages of both agents should have less systemic cytotoxic effect on normal cells, and thus have less side effects on the patient being treated.

Decitabine may be supplied as sterile powder for injection, together with buffering salt such as potassium dihydrogen and pH modifier such as sodium hydroxide. This formulation is preferably stored at 2–8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4–6 hours for delivery of maximum potency.

Potential hematopoietic toxicity associated with cytotoxic anticancer drugs may be reduced by using hematopoietic growth factors, such as G-CSF or GM-CSF. Alternatively, normal hematopoietic stem cells may be protected from drug-induced toxicity by using gene therapy. For example, human cytidine deaminase cDNA may be transferred into the hematopoietic stem cells to protect them from cytotoxicity of decitabine. Cytidine deaminase catalyzes the deamination of cytosine nucleotides and related analog. The deamination of cytosine nucleotide analog such as decitabine results in a loss of their pharmacological activity.

The inventive combination of therapeutic agents may be used in the form of kits. The arrangement and construction of such kits is conventionally known to one of skill in the art. Such kits may include containers for containing the inventive combination of therapeutic agents and/or compositions, and/or other apparatus for administering the inventive combination of therapeutic agents and/or compositions.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method for treating a cancer patient, comprising:
   administering to the cancer patient decitabine at a dose ranging from 1 mg/m$^2$ per day to 20 mg/m$^2$ per day, in combination with a therapeutically effective amount of an anti-neoplastic agent whose activity as an anti-neoplastic agent in vivo is adversely affected by aberrant DNA methylation, wherein the cancer is selected from the group consisting of ovarian, breast, prostate, gastric, lung, pancreas and colon cancer and is refractory to the treatment of the anti-neoplastic agent alone.

2. A method for treating a cancer patient, comprising:
   administering to the cancer patient decitabine at a dose ranging from 1 mg/m$^2$ per day to 20 mg/m$^2$ per day, in combination wit a therapeutically effective amount of an anti-neoplastic agent whose activity as an anti-neoplastic agent in vivo is adversely affected by aberrant DNA methylation, wherein the cancer is a non-small cell lung cancer.

3. The method of claim 1, wherein the anti-neoplastic agent is cisplatin or carboplatin.

4. The method of claim 1, wherein decitabine is administered subcutaneously or intravenously.

5. The method of claim 1, wherein decitabine is administered to the patient intravenously per day at a dose ranging from 5 to 20 mg/m$^2$.

6. A method for treating a cancer patient, comprising:
   administering intravenously to the cancer patient decitabine at a dose ranging from 1 mg/m$^2$ per day to 20 mg/m$^2$ per day, for at lease 3 days per treatment cycle, in combination with a therapeutically effective amount of an anti-neoplastic agent whose activity as an anti-neoplastic agent in vivo is adversely affected by aberrant DNA methylation, wherein the cancer is selected from the group consisting of ovarian, breast, prostate, gastric, lung, pancreas and colon cancer and is refractory to the treatment of the anti-neoplautic agent alone.

7. The method of claim 1, wherein decitabine is administered prior to the administration of the anti-neoplastic agent.

8. A method of claim 2, wherein the anti-neoplastic agent is cisplatin or carboplatin.

9. A method of claim 2, wherein decitabine is administered to the patient intravenously.

10. A method of claim 2, wherein decitabine is administered to the patient intravenously, at a dose ranging from 5 mg/m$^2$ to 20 mg/$^2$, per day.

11. A method of claim 2, wherein decitabine is administered prior to the administration of the anti-neonlastic agent.

12. A method of claim 6, wherein the anti-neoplastic agent is cisplatin or carboplatin.

13. A method of claim 6, wherein decitabine is administered prior to the administration of the anti-neoplastic agent.

* * * * *

UNITED STATES PATENT AND TRADEMARK OFFICE
CERTIFICATE OF CORRECTION

PATENT NO. : 6,613,753 B2
DATED : September 2, 2003
INVENTOR(S) : Rubinfeld et al.

It is certified that error appears in the above-identified patent and that said Letters Patent is hereby corrected as shown below:

<u>Title page,</u>
Item [57], ABSTRACT,
Line 3, "storing" should be amended to -- re-storing --.

<u>Column 5,</u>
Line 47, "neuronms" should be amended to -- neuromas --.
Line 49, "leiomyomater" should be amended to -- leiomyoma --.

<u>Column 8,</u>
Line 6, "losss" should be amended to -- loss --.

<u>Column 9,</u>
Line 50, "Substistuting" should be amended to -- Substituting --.

<u>Column 11,</u>
Line 51, "transription" should be amended to -- transcription --.

<u>Column 16,</u>
Line 24, "occuring" should be amended to -- occurring --.

<u>Column 17,</u>
Line 18, "neuronms" should be amended to -- neuromas --.
Line 19, "ganglloneuromas" should amended to -- ganglio neuromas --.
Line 20, "leiomyamater" should be amended to -- leiomyoma --.

UNITED STATES PATENT AND TRADEMARK OFFICE
CERTIFICATE OF CORRECTION

PATENT NO.    : 6,613,753 B2
DATED         : September 2, 2003
INVENTOR(S)   : Rubinfeld et al.

It is certified that error appears in the above-identified patent and that said Letters Patent is hereby corrected as shown below:

<u>Column 18,</u>
Line 38, "mechanim" should be amended to -- mechanism --.
Line 65, "abostructive" should be amended to -- obstructive --.
Line 66, "disese" should be amended to -- disease --.

Signed and Sealed this

Sixteenth Day of March, 2004

JON W. DUDAS
*Acting Director of the United States Patent and Trademark Office*